United States Patent [19]

Halpern et al.

[11] 4,454,064
[45] Jun. 12, 1984

[54] PROCESS FOR PREPARING PENTAERYTHRITOL PHOSPHATE

[75] Inventors: Yuval Halpern, Skokie, Ill.; Ron H. Niswander, Lake Jackson, Tex.

[73] Assignee: Borg-Warner Corporation, Chicago, Ill.

[21] Appl. No.: 437,789

[22] Filed: Oct. 29, 1982

[51] Int. Cl.³ .............................................. C07F 9/15
[52] U.S. Cl. .................................................... 260/974
[58] Field of Search ............................... 260/936, 974

[56] References Cited

U.S. PATENT DOCUMENTS

| | | | |
|---|---|---|---|
| 3,143,662 | 5/1964 | Gradsten | 71/2.3 |
| 3,155,703 | 11/1964 | Emmons et al. | 260/937 |
| 3,168,548 | 2/1965 | Rätz et al. | 260/936 |
| 3,189,633 | 6/1965 | Chang et al. | 260/937 |
| 3,287,448 | 11/1966 | Rätz et al. | 260/937 |
| 3,293,327 | 12/1966 | Hechenbleikner et al. | 260/936 |
| 3,342,903 | 9/1967 | Grabhofer et al. | 260/927 |

*Primary Examiner*—Anton H. Sutto
*Attorney, Agent, or Firm*—Joseph Shekleton

[57] ABSTRACT

A process involving the reaction of pentaerythritol with phosphorus oxychloride. A solvent is used in the process, but not catalyst or amine (as a hydrogen chloride acceptor) is required.

4 Claims, No Drawings

PROCESS FOR PREPARING PENTAERYTHRITOL PHOSPHATE

The invention of this application relates as indicated to a chemical process and in particular to a process for preparing pentaerythritol phosphate. Still more particularly it relates to such a process that is convenient and produces good yields of relatively pure product.

BACKGROUND OF THE INVENTION

Pentaerythritol phosphate is a white solid melting at 213°–218° C. It is characterized by the structure

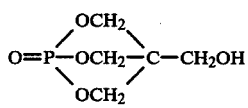

It is a useful intermediate in the preparation of flame-retardant materials, polyurethanes, and plasticizers.

It is well-known in the art that 3,9-dichloro-2,4,8-10-tetraoxa-3,9-diphosphaspiro [5,5]undecane-3,9-dioxide may be prepared

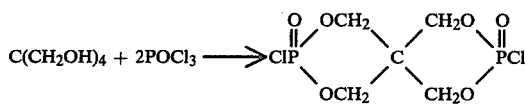

by the reaction of pentaerythritol with two mols of phosphorus oxychloride. See U.S. Pat. No. 3,342,903 (Grabhofer et al.).

U.S. Pat. No. 3,155,703 (Emmons et al.) shows the reaction of trimethylol propane with phosphorous oxychloride, at room temperature, to form a tan semicrystalline mixture which upon crystallization from water yields 51% of a light tan crystalline precipitate. The product is ethyl bicyclic phosphate.

U.S. Pat. No. 3,189,633 (Chang et al.) shows the same reaction, but carried out in the presence of a substantial quantity of pyridine as a hydrogen chloride acceptor. Also, the use of a petroleum ether as a solvent is shown.

U.S. Pat. No. 3,134,662 (Gradsten) shows the reaction of trimethylol propane with thiophosphoryl chloride to produce trimethylolpropane thiophosphate. Benzene is employed as a solvent, the yield of a product is about 35–40%.

U.S. Pat. No. 3,287,448 (Ratz) teaches the preparation of 1-hydroxymethyl-4-phospha-3,5,8-trioxabicyclo [2,2,2]octane-4-sulfide, i.e., pentaerythritol and thiophosphoryl chloride. The reactants are mixed and heated at 160°–170° for six hours. A 63% yield of the product is obtained.

The oxidation of pentaerythritol phosphite to pentaerythritol phosphate is shown in U.S. Pat. No. 3,293,327 (Hechenbleikner et al.). The oxidation is accomplished with hydrogen peroxide, in isopropanol.

In all of these prior art processes, however, the yield of product is low, or it is necessary to use large amounts of a hydrogen-chloride acceptor (such as pyridine), or the product contains sulfur, or the process requires the availability of a relatively expensive starting material (pentaerythritol phosphite). None of these disadvantages inheres in the process of the present invention.

SUMMARY OF THE INVENTION

The invention of the present application is a process for the preparation of pentaerythritol phosphate comprising mixing approximately equimolar amounts of pentaerythritol and phosphorus oxychloride, in a solvent, heating the mixture at a temperature within the range of from about 75° C. to about 125° C., cooling said mixture to precipitate pentaerythritol phosphate, and isolating said pentaerythritol phosphate.

DETAILED DESCRIPTION OF THE INVENTION

A solvent is desirable. The only requirement is that the solvent be inert in the reaction environment. Dioxane is a preferred solvent; ethylene glycol dimethyl ether, diethylene glycol dimethyl ether, chlorobenzene, toluene, xylene, acetonitrile, sulfolane and tetrachloroethylene, are illustrative examples of other suitable solvents. Mixtures of solvents may be used in certain situations.

It is important that approximately stoichiometric quantities of reactants be used because each reactant is polyfunctional. An excess of either pentaerythritol or phosphorous oxychloride results in reduced yields of the pentaerythritol phosphate.

No catalyst is required. The reaction proceeds smoothly merely upon mixing the reactants at the indicated temperature. Nor are large quantities of a hydrogen chloride acceptor, such as an amine, required. This greatly facilitates the process of isolating the desired product, and, of course, makes the process of the invention relatively inexpensive.

The temperature should, as indicated, be within the range of from about 75° C. to about 125° C. It follows that the more desirable solvents are those boiling at least as high as 75° C. A still more limited class of solvents are those which boil within the above range.

Isolation of the product of the process is accomplished merely by permitting the reaction mixture to cool whereupon the desired product, where the solvent is dioxane, for example, precipitates from solution and is collected on a filter. With some other solvents the pentaerythritol phosphate may be sufficiently soluble as to require concentration of the reaction mixture prior to filtration, or even concentration to substantial dryness.

The filtrate can be used in subsequent reactions and, in fact, this is a preferred overall manner of carrying out a series of such reactions, i.e., by re-using the filtrate from one reaction in the next reaction. Yields are increased significantly in this fashion.

The yield of product is high, ranging up almost to 100 percent of the theory, depending to a large extent on the solvent used, although in no instance has a yield of much less than 90 percent been obtained.

The process is illustrated by the following example.

EXAMPLE 1

To a 2,000-ml., three-necked, round bottom flask equipped with mechanical stirrer, reflux condenser, therometer, addition funnel, and dry nitrogen inlet and outlet, there are added 1,050 ml. of dioxane and 210 g. (1.54 mols) of pentaerythritol. The resulting slurry is stirred under a stream of nitrogen and heated to 95° C. whereupon 118 g. (0.77 mol) of phosphorus oxychloride is added. An additional 118 g. (0.77 mol) of phosphorus oxychloride then is added at such a rate as to keep the rate of hydrogen chloride evaluation at less than 2.0 percent/minute. After about six hours 92 percent of the theoretical quantity of hydrogen chloride is evolved. During this period the slurry becomes clear and then solid product begins to settle out. The reaction mixture is allowed to cool to room temperature whereupon more solid is precipitated and the cooled mixture is filtered. The white solid is washed with 150 ml. of dioxane and twice with 300 ml. of hexane, then dried at 70° C. in vacuo to a constant weight (249 g., 89.6 percent of the theory). M.P., 205°–211° C. IR and High Performance Liquid Chromatographic analyses, with respect to an authentic sample, establish the product as pentaerythritol phosphate.

EXAMPLE 2

The procedure of Example 1 is repeated using the filtrate from the filtration step of that example as the solvent. This recycling of the dioxane solvent is repeated several times, with the following results:

| Run No. | Yield | M.P. |
| --- | --- | --- |
| 2 (first recycle) | 93% | 190–205° C. |
| 3 (second recycle) | 95% | 195–205° C. |
| 4 (third recycle) | 98% | 190–200° C. |
| 5 (fourth recycle) | 70%* | 213–218° C. |

*after recrystallization from ethanol.

All parts and percentages herein are by weight unless otherwise expressly stated.

We claim:

1. A process for the preparation of pentaerythritol phosphate comprising mixing approximately equimolar amounts of pentaerythritol and phosphorous oxychloride, in dioxane as a solvent, heating the mixture at a temperature within the range of from about 75° C. to about 125° C., and isolating said pentaerythritol phosphate.

2. The process of claim 1 wherein the phosphorous oxychloride is added portionwise to the pentaerythritol at the reaction temperature.

3. The process of claim 1 wherein the pentaerythritol phosphate is isolated by filtration.

4. The process of claim 3 wherein the filtrate from the isolation step of a prior process is used as the solvent.

* * * * *